US00PP28138P3

(12) United States Plant Patent
Telch

(10) Patent No.: US PP28,138 P3
(45) Date of Patent: Jun. 27, 2017

(54) RASPBERRY PLANT VARIETY NAMED 'ENROSADIRA'

(50) Latin Name: ***Rubus idaeus* L.**
Varietal Denomination: Enrosadira

(71) Applicant: AZ. AGR. Molari & Gatti Di Molari Gilberto, Cesena (IT)

(72) Inventor: Aldo Telch, Faver (IT)

( * ) Notice: Subject to any disclaimer, the term of this patent is extended or adjusted under 35 U.S.C. 154(b) by 117 days.

(21) Appl. No.: 14/120,026

(22) Filed: Apr. 16, 2014

(65) Prior Publication Data

US 2014/0317798 P1 Oct. 23, 2014

(30) Foreign Application Priority Data

Apr. 17, 2013 (QZ) ..... PBR 20131117

(51) Int. Cl.
*A01H 5/08* (2006.01)

(52) U.S. Cl.
USPC ..... Plt./204
CPC ..... *A01H 5/0887* (2013.01)

(58) Field of Classification Search
USPC ..... Plt./204
See application file for complete search history.

(56) References Cited

U.S. PATENT DOCUMENTS

PP20,841 P3 * 3/2010 Pititto ..... Plt./204

* cited by examiner

*Primary Examiner* — June Hwu
(74) *Attorney, Agent, or Firm* — LeClairRyan, a Professional Corporation

(57) ABSTRACT

The red raspberry cultivar 'Enrosadira' was found in Trentino (Italy). The new cultivar is a primocane fruit-bearing variety producing two crops per year, wherein the fruits ripen on current season's cane in the middle of July and on previous season's cane in the beginning of June. The resulting fruits are conical and brilliant light red with a very good taste.

1 Drawing Sheet

BACKGROUND OF THE NEW VARIETY

The present invention concerns a new and distinct cultivar of red raspberry, botanical taxon *Rubus idaeus* L., hereinafter referred to by the cultivar name 'Enrosadira'.

The new cultivar 'Enrosadira' was discovered in 2004 at Faver (Cembra Valley, Province of Trento, Region Trentino—Italy) and has been asexually reproduced by root cutting since 2008. The new variety 'Enrosadira' was produced by pollination of varieties T44L04 'Lagorai' (female parentage)×T35L04 (male parentage). The new cultivar was found to be stable and its distinctive characteristics have been transmitted without change through succeeding (more than 98%) asexual propagations.

SUMMARY OF THE INVENTION

The most outstanding and distinguishing characteristics of the new 'Enrosadira' cultivar are briefly reported hereunder:

primocane fruit-bearing raspberry plant;
brilliant light red fruit colour and good flavour;
large, conical, and firm berries;
fruit having a very good shelf-life;
tolerance to raspberry pests and diseases.

The new cultivar can be propagated by the use of suckers produced in a spawn-bed, root cutting, and use of tissue culture techniques. Propagation by root cutting is preferred.

BRIEF DESCRIPTION OF THE DRAWINGS

The new red raspberry cultivar 'Enrosadira' is illustrated by the accompanying drawings, which are color photographs showing typical specimens of the new variety. The photographs are of 'Enrosadira' raspberry two year old plants.

DETAILED DESCRIPTION OF THE NEW CULTIVAR

Figure 1:
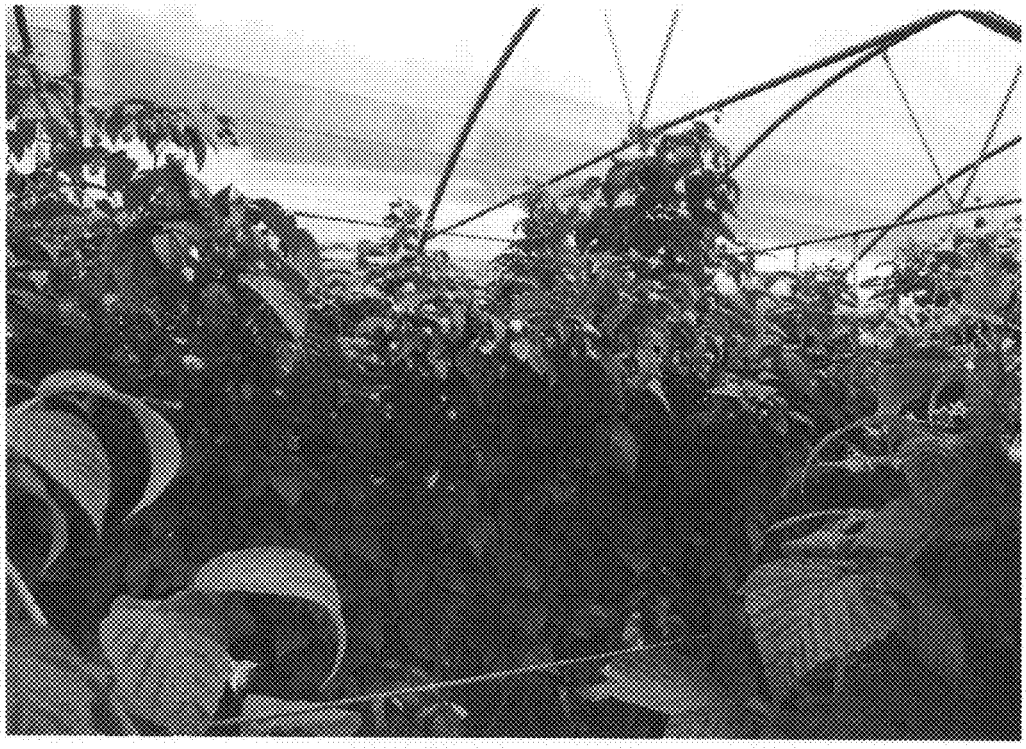
FIG. 1 is a color photograph of an 'Enrosadira' raspberry plant of the present invention in a planted row showing the plant's general characteristics, including a typical distribution of fruits and leaf morphology.
Figure 2:
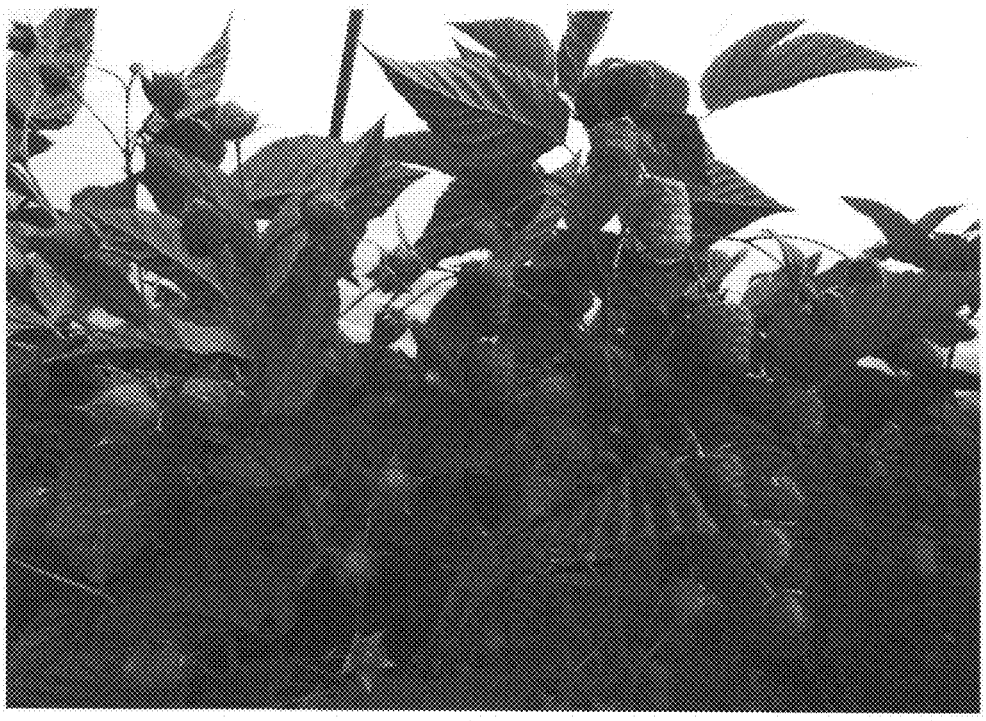
FIG. 2 is a color photograph of an 'Enrosadira' raspberry plant of the present invention showing both the ripe and immature fruit size, color, and shape.

The following detailed description sets forth the distinctive characteristics of the new raspberry variety 'Enrosadira'.

The performance of the new cultivar for retention of its distinctive characteristics was evaluated through successive asexual propagations by root cutting at Faver (Cembra Valley, Province of Trento, Region Trentino—Italy) under conditions of temperature ranging from −8° C. in winter in an open greenhouse to 32° C. in summer in a closed greenhouse. The plants were grown in a peat substrate as soil.

A plant assessment was performed for four years.

The general characteristics of the new variety 'Enrosadira' are: upright canes, strong vigor, adapted to the medium-high winter chill conditions of Northern Italy, and very good root system. The floral bloom is simple with short laterals; the blooming begins in summer on the current year's shoots and in the spring season on the previous year's canes.

The 'Enrosadira' is a very early primocane fruit-bearing variety with fruit production beginning in early summer (June in Northern Italy) and lasting until autumn (September in Northern Italy). In autumn, the fruit production is small compared to early summer.

Color references are primarily made to R.H.S. Colour Chart of The Royal Horticultural Society of London.

Classification:
- *Family.*—Rosaceae.
- *Botanical taxon.*—*Rubus idaeus* L.
- *Common name.*—Rasperry.

Parentage: Pollination of the raspberry variety plants T44L04 'Lagorai' (female parent) with T35L04 (male parent) raspberry plants.

Plant:
- *Average height.*—175 cm.
- *Spread (average).*—60 cm.
- *Shape.*—Upright canes.

Primocane:
- *Cane color.*—Green (group RHS 142C).
- *Average length.*—175 cm.
- *Average diameter.*—5 cm.
- *Texture.*—Little thorny.
- *Current season's vegetative bud cane length.*—Medium.
- *Current season's cane internode length.*—Medium.
- *Number of current season's shoots.*—Average number 22.
- *Very young shoot.*—Anthocyanin coloration at apex during rapid growth is absent.
- *Previous season's cane colour.*—Greyed-Orange (RHS 177A).

Floricane:
- *Cane color.*—Green (group RHS 142C).
- *Average length.*—175 cm.
- *Average diameter.*—6 cm.
- *Texture.*—Little thorny.
- *Internode length.*—Medium.

Spines:
- *Shape.*—Very little, pointy, thick and dense.
- *Size.*—Average length 3-4 mm.
- *Color.*—Brown (group RHS 200A).

Leaves:
- *Type.*—Compound, lanceolate, alternate, petioled, 3-5 leaflets.
- *Leaf average size.*—Length 10-12 cm; width 6-8 cm.
- *Terminal leaflet's average size.*—8-10 cm.
- *Margin type.*—Saw-edged.
- *Shape.*—The leaf apex shape is acuminate and the leaf base shape is rounded.
- *Color.*—Green (group RHS 141B) on the upper surface and Green (group RHS 141C) on the lower surface.
- *Texture.*—The upper surface texture is hairy and the lower surface is a little bit hairy with many veins.

Stipule:
- *Number per leaf.*—2.
- *Shape.*—Erect.
- *Size.*—Average length 4-5 mm.
- *Color.*—Yellow-green (RHS 144A).

Flowers:
- *Type.*—Raceme.
- *Shape.*—Rotate.
- *Size.*—Average length 1 cm; average diameter 0.4 inches.
- *Color.*—White (group RHS 155B).

Petals:
- *Average size.*—Length 7-8 mm; width 3-4 mm.
- *Number.*—5.
- *Color.*—White (group RHS 155B).

Sepals:
- *Size.*—Average length 0.8-1 cm.
- *Number.*—5.
- *Color.*—Green (group RHS 142C).

Peduncles:
- *Size.*—Average length 5 cm.
- *Surface texture.*—Slightly thorny.
- *Color.*—Yellow-green (RHS 144B).

Pedicels:
- *Size.*—Average length 3 cm.
- *Surface texture.*—Slightly thorny.
- *Color.*—Yellow-green (RHS 144D).

Reproductive organs:
- *Pistil average number per flower.*—80-90.
- *Pistil size.*—Average length 3.5 mm.
- *Pistil color.*—White (group RHS 155C).
- *Stamen average number per flower.*—90-95.
- *Stamen size.*—Average length 6 mm.
- *Stamen color.*—White (group RHS 155C).

Fruit:
- *General shape.*—Conical, an aggregate of drupelets.
- *Size.*—Average length 3 cm; average width 1.8-2 cm.
- *Weight.*—6-8 g.
- *Glossiness.*—Strong.
- *Firmness.*—Very soft.
- *Colour of ripe fruit.*—Red (group RHS 47B).
- *Main bearing time.*—Both on previous year's cane in summer and on current year's cane in autumn.
- *Time of beginning the fruit ripening on previous year's cane.*—Very early to early (middle of June in Northern Italy).
- *Time of beginning the fruit ripening on current season's cane.*—Very early (middle of July in Northern Italy).
- *Previous year fruiting lateral attitude in summer.*—Erect.
- *Previous year fruiting lateral length in summer.*—Short.
- *Average weight per plant yield.*—1.4 Kg.
- *Fruit's market use.*—Fresh consumptions, frozen or processed.
- *Shipping conditions.*—Temperature 3° C.
- *Storage.*—Very good shelf life in conditioned storage, yields good quality fruits.

Pest and disease resistance: The new variety 'Enrosadira' is resistant to large raspberry aphid (*Amphorophora idaei*), *Phytophthora fragariae* rubi, and *Didymella applanata.* The new variety 'Enrosadira' is adapted to medium winter chill conditions such as in Northern Italy, having in an open-air environment a hardiness for temperatures from −8° C. to 32° C. The new cultivar 'Enrosadira' is similar to, but distinct from, the commercial variety 'Erika' (U.S. Plant Pat. No. 20,841) as shown in Table 1.

TABLE 1

Comparison between 'Enrosadira' and 'Erika'

| Characteristic | 'Enrosadira' | 'Erika' |
|---|---|---|
| Plant | Medium-high, vigorous | Medium |
| Dormant cane color | Greyed-orange (group RHS 177A) | Greyed-orange (group RHS 174A) |
| Spines | Thick and dense | Thick and dense |
| Fruit | Red (group RHS 47B) Conical | Red (RHS 53A) Broad conical |
| Fruit ripening time on the previous season's cane | Middle of June in Northern Italy | Beginning of July in Northern Italy |

A comparison of the new variety 'Enrosadira' with the female parent 'Lagorai' is shown in Table 2.

TABLE 2

Comparison between 'Enrosadira' and 'Lagorai'

| Characteristic | 'Enrosadira' | 'Lagorai' |
|---|---|---|
| Plant | Medium-high, vigorous | Medium |
| Dormant cane color | Greyed-orange (group RHS 177A) | Greyed-orange (group RHS 177D) |
| Spines | Thick and dense | Thick and sparse |
| Fruit | Red (group RHS 47B); Conical | Red (group RHS 46B) Conical |

TABLE 2-continued

Comparison between 'Enrosadira' and 'Lagorai'

| Characteristic | 'Enrosadira' | 'Lagorai' |
|---|---|---|
| Fruit ripening time on the previous season's cane | Middle of June in Northern Italy | Beginning of July in Northern Italy |

A comparison of the new variety 'Enrosadira' with the male parent T35L04 is shown in Table 3.

TABLE 3

Comparison between 'Enrosadira' and T35L04

| Characteristic | 'Enrosadira' | T35L04 |
|---|---|---|
| Plant | Medium-high, vigorous | Medium vigorous |
| Dormant cane color | Greyed-orange (group RHS 177A) | Brown (group RHS 200D) |
| Spines | Thick and dense | Absent |
| Fruit | Red (group RHS 47B); Conical | Dull Red (group RHS 45B) Conical |
| Fruit ripening time on the previous season's cane | Middle of June in Northern Italy | Beginning of July in Northern Italy |

What is claimed:

1. A new and distinct cultivar of red raspberry plant named 'Enrosadira' substantially as herein shown and described.

* * * * *